United States Patent [19]

Antosz et al.

[11] 4,029,549

[45] June 14, 1977

[54] PROCESS OF PRODUCING 9α-HYDROXY-3-KETOBISNORCHOL-4-EN-22-OIC WITH MYCOBACTERIUM FORTUITUM

[75] Inventors: Frederick J. Antosz; Willard J. Haak; Merle G. Wovcha, all of Kalamazoo, Mich.

[73] Assignee: The Upjohn Company, Kalamazoo, Mich.

[22] Filed: Apr. 30, 1976

[21] Appl. No.: 681,789

Related U.S. Application Data

[63] Continuation-in-part of Ser. No. 670,657, March 26, 1976, abandoned.

[52] U.S. Cl. .............................................. 195/51 S
[51] Int. Cl.$^2$ ........................................ C12D 13/02
[58] Field of Search ............... 260/397.1; 195/51 S, 195/51 R

[56] References Cited

UNITED STATES PATENTS

| | | | |
|---|---|---|---|
| 2,602,769 | 7/1952 | Murray et al. .................... | 195/51 A |
| 3,031,472 | 4/1962 | Bernstein et al. ............... | 260/397.4 |
| 3,684,657 | 8/1972 | Kraychy ........................... | 195/51 G |
| 3,759,791 | 9/1973 | Marsheck et al. ............... | 195/51 G |

OTHER PUBLICATIONS

Mamoli et al., Ber. 70, 470–471 (1937).
Mamoli et al., Ber. 70, 2079–2082 (1937).

*Primary Examiner*—Lionel M. Shapiro
*Attorney, Agent, or Firm*—Roman Saliwanchik

[57] ABSTRACT

The novel compound 9α-hydroxy-3-ketobisnorchol-4-en-22-oic, hereinafter referred to as 9α-OH BN acid. This compound is producible in a fermentation using the microorganism *Mycobacterium fortuitum*, NRRL B-8119. 9α-OH BN acid can be used as an intermediate to make useful steroids.

15 Claims, No Drawings

PROCESS OF PRODUCING 9α-HYDROXY-3-KETOBISNORCHOL-4-EN-22-OIC WITH MYCOBACTERIUM FORTUITUM

CROSS REFERENCE TO RELATED APPLICATION

This is a continuation-in-part of our pending application Ser. No. 670,657 filed on Mar. 26, 1976, and now abandoned.

BACKGROUND OF THE INVENTION

The transformation of steroids by microorganisms has been widely studied and documented. Apparently, the earliest such work was by Mamoli and Vercellone in 1937, Ber. 70, 470 and Ber. 70, 2079. They disclosed the reduction of 17-ketosteroids to 17β-hydroxysteroids by fermenting yeast. More recently, Peterson and Murray disclosed the 11α-hydroxylation of progesterone with the fungus Rhizopus nigricans: see, U.S. Pat. No. 2,602,769 (1952). Also recently, Kraychy et al. in U.S. Pat. No. 3,684,657 (1972) discloses the selective microbiological degradation of steroidal 17-alkyls by fermenting a steroid containing at least 8 carbons in the 17-alkyl side chain with Mycobacterium sp. NRRL B-3683 to prepare androst-4-ene-3,17-dione, androst-1,4-diene-3,17-dione, and 20α-hydroxymethyl-pregna-1,4-dien-3-one. Even more recently, Marsheck et al. in U.S. Pat. No. 3,759,791 (1973) disclose the selective microbiological prepartion of androst-4-ene-3,17-dione by fermenting a steroid of the cholestane or stigmastane series containing at least 8 carbons in the 17-alkyl side chain with Mycobacterium sp. NRRL B-3805.

BRIEF SUMMARY OF THE INVENTION

9α-OH BN acid, a novel compound, is produced in a fermentation process using the microorganism *Mycobacterium fortuitum*, NRRL B-8119. This microorganism is characterized, in part, by its ability to selectively degrade steroids having 17-alkyl side chains of from 8 to 10 carbon atoms, inclusive, and accumulate 9α-hydroxyandrostenedione, hereinafter referred to as 9α-OH AD, and 9α-OH BN acid in the fermentation beer. Other mutants of Mycobacterium, as well as of the following genera of microorganisms, can be used in the subject invention so long as they have the ability to selectively degrade steroids having 17-alkyl side chains of from 8 to 10 carbon atoms, inclusive, and accumulate 9α-OH AD and 9α-OH BN acid in the fermentation beer. The genera of microorganisms which are within the scope of the subject invention are Arthrobacter, Bacillus, Brevibacterium, Corynebacterium, Microbacterium, Mycobacterium, Nocardia, Protaminobacter, Serratia, and Streptomyces. The preferred genera is Mycobacterium. Exemplary species of this genera are *M. phlei*, *M. smegmatis*, *M, rhodochrous*, *M. mucosum*, *M. fortuitum*, and *M. butyricum*. Specifically exemplified herein is the mutant microorganism, *Mycobacterium fortuitum*, NRRL B-8119. Procedures are disclosed herein for mutating microorganisms of the above genera to give the desired mutants. Examples of suitable steroid substrates are sitosterols, cholesterol, stigmasterol, campesterol, and like steroids with 17-alkyl side chains of from 8 to 10 carbon atoms, inclusive. These steroid substrates can be in either the pure or crude form.

DETAILED DESCRIPTION OF THE INVENTION

The Microorganisms

Mutants which are characterized by their ability to selectively degrade steroids having 17-alkyl side chains of from 8 to 10 carbon atoms, inclusive, and accmulate 9α-OH AD and 9α-OH BN acid in the fermentation beer can be obtained by mutating microorganisms of the following genera: Arthrobacter, Bacillus, Brevibacterium, Corynebacterium, Microbacterium, Mycobacterium, Nocardia, Protaminobacter, Serratia, and Streptomyces. Mycobacterium fortuitum, ATCC 6842, has been mutated, as disclosed herein, to give a novel laboratory mutant microorganism. The 1974 ATCC Catalogue discloses the following alongside the listing of ATCC 6842: "J. C. Cruz 2. Cold abscess. Acta Med. Rio de Janeiro 1:1 (1936). Medium 90 37C". *M. fortuitum*, ATCC 6842, degrades sterols non-selectively to small molecular weight compounds, e.g. $CO_2 + H_2O$. Thus, this microorganism is not suitable as a selective steroid degrader.

Mutation of *M. fortuitum*, ATCC 6842, using nitrosoguanidine has resulted in the production of a mutant which selectively degrades steroids having 17-alkyl side chains of from 8 to 10 carbon atoms, inclusive, to produce 9α-OH AD and 9α-OH BN acid. This mutant microorganism of *M. fortuitum* has been given the accession number NRRL B-8119, by the Nothern Regional Research Laboratory, U.S. Department of Agriculture, Peoria, Illinois, U.S.A., where it has been deposited in the permanent collection. A subculture of this microorganism is freely available from this depository by request made thereto. It should be understood that the availability of the culture does not constitute a license to practice the subject invention in derogation of patent rights granted with the subject instrument by governmental action.

The morphology and drug sensitivities of *M. fortuitum*, NRRL B-8119, are indistinguishable from that of the parent *M. fortuitum*, ATCC 6842. Both *M. fortuitum* cultures are acid-fast non-motile, non-spore-forming bacilli belonging to the family Mycobacteriaceae of the order Actinomycetales. According to Runyons classification, Runyon, E. H. 1959 Med. Clin. North America 43:273, it is a nonchromogenic group IV mycobacterium, i.e., it grows rapidly at low temperature to produce nonpigmented colonies on relatively simple media.

*M. fortuitum* ATCC 6842 and *M. fortuitum* NRRL B-8119, are clearly distinguishable in their action on steroid molecules. As disclosed above, *M. fortuitum* ATCC 6842 is a non-selective degrader of steroids, whereas *M. fortuitum* NRRL B-8119 is a selective degrader. This property of *M. fortuitum* NRRL B-8119 makes it highly useful, as disclosed herein.

The mutation of *M. fortuitum* ATCC 6842 to give *M. fortuitum* NRRL B-8119 was accomplished by the use of nitrosoguanidine. The details of the procedure are described infra. Though mutation procedures are generally known in the art, there is no known art which teaches or even suggests the type of mutants, if any, which might be obtained by use of the subject mutation procedure. Also, though the mutation and transformation procedures, disclosed herein, are detailed for a Mycobacterium, it should be understood that similar or equivalent procedures can be used with microorganisms of the other genera, as disclosed herein.

The Transformation Process

The selective transformation of the subject invention can be effected in a growing culture of *M. fortuitum* NRRL B-8119 by either adding the selected steroid substrate to the culture during the incubation period, or incorporating it in the nutrient medium prior to inoculation. The steroid can be added singly or in combination with another steroid. The preferred, but not limiting, range of concentration of the steroid in the culture is about 0.1 to about 100 grams per liter. The culture is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, ammonium salts and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

The transformation process can range from about 72 hours to 15 days. The incubation temperature during the transformation process can range from about 25° C. to about 37° C., with 30° C. being preferred. The contents of the transformation vessel are aerated with sterilized air and agitated to facilitate growth of the microorganism, and, thus, enhance the effectiveness of the transformation process.

Upon completion of the transformation process, as evidenced by thin layer chromatography using silica gel plates (E. Merck, Darmstadt) and a solvent system consisting of 2:3 (by volume) ethyl acetate-cyclohexane, the desired transformed steroid is recovered by means well known in the art. For example, the fermentation (transformation) reaction mixture, including the fermentation liquor and cells, can be extracted with a water-immiscible organic solvent for steroids. Suitable solvents are methylene chloride (preferred), chloroform, carbon tetrachloride, ethylene chloride, trichloroethylene, ether, amyl acetate, benzene and the like.

Alternatively, the fermentation liquor and cells can be first separated by conventional methods, e.g., filtration or centrifugation, and then separately extracted with suitable solvents. The cells can be extracted with either water-miscible or water-immiscible solvents. The fermentation liquor, freed of cells, can be extracted with water-immiscible solvents.

Pooled extracts of the beer can be washed with a solution to remove acidic products, one fourth volume of a 5% sodium bicarbonate solution is preferred, to remove the 9α-OH BN acid. Other mineral base solutions can be used so long as the pH is over 8.0. 9α-OH BN acid can be obtained in a purified form by extracting the wash solution twice with a water-immiscible organic solvent for steroids, butyl acetate (¼ volume per wash) is preferred, and crystallizing the 9α-OH BN acid by concentrating the extracts. Other water-immiscible organic solvents for steroids, as described above, can be used in place of the butyl acetate.

9α-OH AD can be recovered from the fermentation beer extracts, described above, by first filtering the extracts through diatomaceous earth and then drying the filtrate in vacuo. The resulting residue containing the desired transformed steroid then can be dissolved in 10% chloroform in methanol and this then concentrated with nitrogen on a steam bath until crystals appear. The solution then can be cooled to room temperature and filtered to remove precipitated steroid.

9α-OH BN acid can be chemically converted into known useful steroid intermediates by methods known in the art. For example, treatment with diazomethane results in the conversion of the 22-carboxyl group to a methyl ester. The resulting compound can then be converted to 9(11)-dehydro BN acid by treatment with N-bromoacetamide and sulfur dioxide in pyridine, as disclosed in British Pat. No. 869,815, followed by hydrolysis to regenerate the 22-carboxyl. 9(11)-Dehydro BN acid can be converted to 9(11)-dehydroprogesterone by, for example, the method described in Ber. 88: 883 (1955), and subsequently to 11β-hydroxyprogesterone as described in JACS 88: 3016 (1966). Treatment of 11β-hydroxyprogesterone with chromic acid yields 11-ketoprogesterone which is a known intermediate in the synthesis of cortisol acetate, a major and highly active cortical steroid [see, for example, Fieser and Fieser, Steroids, page 676, Reinhold (1959)].

The following examples are illustrative of the process and products of the subject invention but are not to be construed as limiting. All percentages are by weight and all solvent mixture proportions are by volume unless otherwise noted.

EXAMPLE 1

Prepgration of Mutant *M. fortuitum* NRRL B-8119 From *M. fortuitum* ATCC 6842.

a. Nitrosoquanidine Mutagenes is
Cells of *M. fortuitum* ATCC 6842 are grown at 28° C. in the following sterile seed medium:

| | |
|---|---|
| Nutrient Broth (Difco) | 8 g/liter |
| Yeast Extract | 1 g/liter |
| Glycerol | 5 g/liter |
| Distilled Water, q.s. | 1 liter |

The pH is adjusted to 7.0 with 1N NaOH prior to sterilization at 121° C. for 20 minutes.

The cells are grown to a density of about 5 × 10⁸ per ml, pelleted by centrifugation, and then washed with an equal volume of sterile 0.1 M sodium citrate, pH 5.6. Washed cells are resuspended in the same volume of citrate buffer, a sample removed for titering (cell count), and nitrosoguanidine added to a final concentration of 50 μg/ml. The cell suspension is incubated at 37° C. in a water bath for 30 minutes, after which a sample is again removed for titering and the remainder centrifuged down and washed with an equal volume of sterile 0.1 M potassium phosphate, pH 7.0. Finally, the cells are resuspended in a sterile minimal salts medium, minus a carbon source, consisting of the following:

| | |
|---|---|
| NH₄NO₃ | 1.0 g/liter |
| K₂HPO₄ | 0.25 g/liter |
| MgSO₄ . 7H₂O | 0.25 g/liter |
| NaCl | 0.005 g/liter |
| FeSO₄ . 7H₂O | 0.001 g/liter |
| Distilled Water, q.s. | 1 liter |

The pH is adjusted to 7.0 with 1N HCl prior to sterilization at 121° C. for 20 minutes. The cells are then plated out to select for mutants.

b. Selection And Isolation Of Mutant *M. fortuitum* NRRL B-8119.

Mutagenized cells, as described above, are diluted and spread onto plates containing a medium consisting of the following (modified from Fraser and Jerrel. 1963. J. Biol. Chem. 205:291–295):

| Glycerol | 10.0 g/liter |
| --- | --- |
| $K_2HPO_4$ | 0.5 g/liter |
| $NH_4Cl$ | 1.5 g/liter |
| $MgSO_4 . 7H_2O$ | 0.5 g/liter |
| $FeCl_3 . 6H_2O$ | 0.05 g/liter |
| Distilled Water, q.s. | 1 liter |

The pH is adjusted to 7.0, agar (15 g/liter) is added, and the medium is autoclaved at 121° C. for 30 minutes and then poured into sterile Petri plates.

Growth on this medium eliminates most nutritional auxotrophes produced by the mutagensis procedure, e.g., cultures that require vitamins, growth factors, etc. in order to grow on chemically defined medium are eliminated. After incubation at 28° C. for about 7 days, the resulting colonies are replicated to test plates suitable for selecting mutants and then back onto control plates containing the glycerol-based medium. The test plates are prepared as described by Peterson, G. E., H. L. Lewis and J. R. Davis. 1962. "Preparation of uniform dispersions of cholesterol and other water-insoluble carbon sources in agar media." J. Lipid Research 3:275–276. The minimal salts medium in these plates is as described above in section (a) of Example 1. Agar (15 g/liter), and an appropriate carbon source (1.0 g/liter), such as sitosterol or androstenedione (AD), are added and the resulting suspension autoclaved for 30 minutes at 121° C. The sterile, hot mixture is then poured into a sterile blender vessel, blended for several minutes, and then poured into sterile Petri plates. Foaming tends to be a problem in this procedure but can be reduced by blending when the mixture is hot and by flaming the surface of the molten agar plates. In this manner uniform dispersions of water-insoluble carbon sources are obtained which facilitates the preparation of very homogenous but opaque agar plates.

Colonies which grew on the control plates, but not on test plates containing AD as the sole carbon source, are purified by streaking onto nutrient agar plates. After growth at 28° C., individual clones are picked from the nutrient agar plates with sterile toothpicks and retested by inoculating grided plates containing AD as the carbon source. Purified isolates which still exhibit a phenotype different from the parental culture are then evaluated in shake flasks.

c. Shake Flask Evaluation

Shake flasks (500 ml) contain 100 ml of biotransformation medium consisting of the following ingredients:

| Glycerol | 10.0 g/liter |
| --- | --- |
| $K_2HPO_4$ | 0.5 g/liter |
| $NH_4Cl$ | 1.5 g/liter |
| $MgSO_4 . 7H_2O$ | 0.5 g/liter |
| $FeCl_3 . 6H_2O$ | 0.05 g/liter |
| Distilled Water, q.s. | 1 liter |

Soyflour (1 g/liter) is blended into the medium and then sitosterol (10 g/liter) is also blended into the medium. After the flasks are autoclaved for 20 minutes at 121° C., they are cooled to 28° C. and then inoculated with 10 ml of seed growth prepared as follows:

The purified isolates from part (b) are grown on agar slants at 28° C. A loop of cells taken from a slant is used to inoculate at 500-ml flask containing 100 ml of sterile seed medium consisting of the following ingredients:

| Nutrient Broth (Difco) | 8 g/liter |
| --- | --- |
| Yeast Extract | 1 g/liter |
| Glycerol | 5 g/liter |
| Distilled Water, q.s. | 1 liter |

The pH is adjusted to 7.0 with 1N NaOH prior to autoclaving the flasks at 121° C. for 20 minutes. The seed flasks are incubated at 28° C. for 72 hours.

As disclosed above, 10 ml of seed growth is then used to inoculate each 500-ml flask containing 100 ml of sterile transformation medium. The flasks are then incubated at 28° C. to 30° C. on a rotary shaker and sampled at various intervals. Ten ml samples are removed and extracted by shaking with 3 volumes of methylene chloride. Portions of the extracts are analyzed by thin layer chromatography using silica gel and the solvent system described above, i.e., 2:3 (by volume) ethyl acetatecyclohexane, and by gas-liquid chromatography. Evidence of the presence of 9α-OH AD confirms the selective degradation of sitosterol by the mutant produced from the parent *M. fortuitum* ATCC 6842.

EXAMPLE 2

Transformation of Sitosterol to 9α-OH AD and 9α-OH BN Acid.

The medium used is the same as in Example 1 (c). This medium is sterilized by heating 30 minutes at 121° C., whereupon it is cooled to 30° C. and then inoculated with 10 parts of a seed culture of the mutant mycobacterium *M. fortuitum* NRRL B-8119, prepared as described in Example 1. The inoculated mixture is incubated at 30° C. for 336 hours with agitation to promote submerged growth. Following incubation, the mixture is acidified and then extracted with methylene chloride. The extract is filtered through diatomaceous earth and the filtrate is vacuum distilled to dryness. The residue is taken up in 10% chloroform in methanol and then concentrated with nitrogen on a steam bath until crystals appear. The solution is then cooled to room temperature and filtered to remove the precipitated sitosterols. From the supernatant, on evaporation of solvent, a good yield of a mixture of crude 9α-OH AD and 9α-OH BN acid is obtained. A trace of 9α-hydroxy-4-androstene-3-one-17 ol is shown by thin layer chromatography to be present.

EXAMPLE 3

By substituting cholesterol, stigmasterol, campesterol for sitosterol in the fermentation, as described in Example 2, there is produced 9α-OH AD and 9α-OH BN acid.

EXAMPLE 4

By adding a combination of any of the steroids in Example 3, in addition to sitosterol, or in place of sitosterol, in Example 2, there is produced 9α-OH AD and 9α-OH BN acid.

EXAMPLE 5

Recovery of 9α-OH BN Acid

9α-OH BN acid is recovered from the fermentation beer produced in Examples 2–4 by the following procedure which also affords a purified preparation of 9α-OH AD. The insolubles are removed from fermentation broth prepared as described in Examples 2–4 by filtration or centrifugation. The separated cake is washed with a suitable amount of water and the wash liquid combined with the solids-free filtrate. The cake fraction is leached with an aqueous acetone solution (1:4), the acetone removed and the resulting aqueous stream combined with the solids-free filtrate and wash. Residual sterols may be recovered from the leached cake fraction by extracting with methylene chloride, removal of the solvent and subsequent crystallization.

The filtered beer fraction is extracted twice with one half volume of butyl acetate at a pH of about 4.0 and then spent beer discarded. Pooled extracts of the beer are washed with one fourth volume of 5% sodium bicarbonate solution to remove the 9α-OH BN acid which is produced in the fermentation. The 9α-OH BN acid is obtained in a purified form free from 9α-OH AD, by extracting the wash solution twice with butyl acetate (¼ volume per wash) and crystallizing the 9α-OH BN acid by concentrating the extracts.

The pooled neutralized extracts are concentrated to about 2% of the beer volume, cooled and the essentially pure 9α-OH AD crystallized. The product is obtained by the usual methods of filtration and drying. This product assays greater than 95% purity by liquid chromatography assay. Additional 9α-OH AD may be obtained from the mother liquors by further concentration and the addition of cyclohexane to reduce the solubility.

EXAMPLE 6

By substituting a microorganism from the genera Arthrobacter, Bacillus, Brevibacterium, Corynebacterium, Microbacterium, Nocardia, Protaminobacter, Serratia, and Streptomyces, in Example 1 for Mycobacterium fortuitum ATCC 6842 there are obtained mutant microoganisms which are characterized by their ability to selectively degrade steroids having 17-alkyl side chains of from 8 to 10 carbon atoms, inclusive, and accumulate 9α-OH AD and 9α-OH BN acid in the fermentation beer.

EXAMPLE 7

By substituting the mutants obtained in Example 6 for M. fortuitum NRRL B-8119 in Examples 2–4, there is produced 9α-OH AD and 9α-OH BN acid.

EXAMPLE 8

By substituting a microoganism selected from the group consisting of Mycobacterium phlei, M. smegmatis, M. rhodochrous, M. mucosum, and M. butyricum for M. fortuitum ATCC 6842 in Example 1 there are obtained mutant microorganisms which are characterized by their ability to selectively degrade steroids having 17-alkyl side chains of from 8 to 10 carbon atoms, inclusive, and accmulate 9α-OH AC and 9α-OH BN acid in the fermentation beer.

EXAMPLE 9

By substituting the mutants obtained in Example 8 for M. fortuitum NRRL B-8119 in Examples 2–4, there is produced 9α-OH AD and 9α-OH BN acid.

9α-OH BN acid can be represented by the following structural formula:

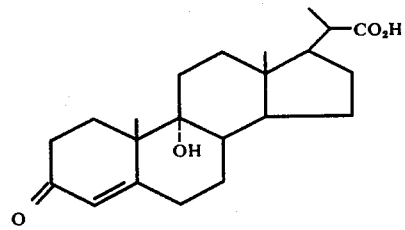

9α-OH BN acid was characterized by spectral data and comparison with bis-nor acid as follows:

The mass spectrum indicated a molecular weight of 360. The strong ion at m/e 124 was indicative of a $\Delta^4$-3-keto-steroid while the ion at m/e 136 suggested the presence of a hydroxyl group at C-9. The infrared spectrum confirmed the presence of a carboxylic acid group (multiple bands between 2800–2500 cm$^{-1}$) and indicated the presence of two carbonyl groups (1740 cm$^{-1}$ - acid C=O; 1665 cm$^{-1}$ - α,β-unsaturated C=O; 1625 cm$^{-1}$ - C=C). The $^1$H-nmr spectrum indicated the presence of three methyl groups: δ 0.73 (singlet), 1.21 (doublet) and 1.31 (singlet). The nmr spectrum also indicated the presence of two exchangeable protons and a single olefinic proton. The presence of three methyl groups suggested that a side chain was present at carbon 17. Based on this data, the material was tentatively identified as 9α-hydroxy bis-nor acid.

A $^{13}$C-nmr spectrum of this material confirmed the presence of 22 carbon atoms which included two carbonyl carbons (δ 197.9 and 177.3), two double-bond carbons (δ 170.8 and 124.9) and a carbon bearing a hydroxyl group (δ 75.1). A comparison was then made with the spectral properties of bis-nor acid. The infrared spectra was similar (2800–2500, 1735, 1655, 1625 cm$^{-1}$). The methyl signals of bis-nor acid occurred at δ 0.75 (C-18), 1.21 (C-19) and 1.22 (C-21) in the $^1$H-nmr spectrum. The downfield shift of the C-19 methyl group by 0.10 ppm in the $^1$H-mnr spectrum of 9α-OH BN acid is consistent with the presence of a hydroxyl group at C-9.

We claim:

1. A process for preparing 9α-hydroxy BN acid which comprises:
   a. cultivating a 9α-hydroxy BN acid producing microorganism in an aqueous nutrient medium under aerobic conditions in the presence of a steroid containing from 8 to 10 carbon atoms, inclusive, in the 17-alkyl side chain to produce 9α-hydroxyandrostenedione and 9α-hydroxy BN acid in the fermentation beer, and,
   b. isolating said 9α-hydroxy BN acid free from 9α-hydroxyandrostenedione.

2. A process, according to claim 1, wherein said 9α-hydroxy BN acid is isolated free from 9α-hydroxyandrostenedione, which comprises:
   a. filtering the fermentation beer to give a filtrate,
   b. extracting said filtrate with a water-immiscible organic solvent for steroids to give an extract, c. washing said extract with an acid-removing solution to give 9α-hydroxy BN acid in a wash solution,
d. extracting said wash solution with a water-immiscible organic solvent for steroids on an extract, and,
e. crystallizing 9α-hydroxy BN acid from said extract by concentration of the extract.

3. A process, according to claim 2, wherein said filtrate is extracted with butyl acetate at a pH of about 4.0.

4. A process, according to claim 3, wherein said extract is washed with a 5% sodium bicarbonate solution.

5. A process, according to claim 4, wherein said wash solution is extracted with butyl acetate.

6. A process, according to claim 1, wherein said 9α-hydroxy BN acid-producing microorganism is a Mycobacterium mutant which is characterized by its ability to selectively degrade steroids having 17-alkyl side chains of from 8 to 10 carbon atoms, inclusive, and accumulate 9α-hydroxyandrostenedione and 9α-hydroxy BN acid in the fermentation beer.

7. A process, according to claim 6, wherein said mutant microorganism is cultivated in an aqueous nitrient medium under aerobic conditions in the presence of a mixture of two or more steroids wherein each steroid contains from 8 to 10 carbon atoms, inclusive, in the 17-alkyl side chain.

8. A process, according to claim 7, wherein said steroid is selected from the group consisting of sitosterol, cholesterol, stigmasterol, and cempersterol.

9. A process, according to claim 8, wherein said steroid mixture is selected from the group consisting of sitosterol, cholesterol, stigmasterol, and cempesterol.

10. A process, according to claim 6, wherein said Mycobacterium mutant is *Mycobacterium fortuitum* NRRL B-8119.

11. A process, according to claim 1, wherein said 9α-hydroxy BN acid-producing microorganism is selected from the group consisting of Arthrobacter, Bacillus, Brevibacterium, Corynebacterium, Microbacterium, Nocardia, Protaminobacter, Serratia, and Streptomyces, said microorganism being characterized by its ability to selectively degrade steroids having 17-alkyl side chains of from 8 to 10 carbon atoms, inclusive, and accumulate 9α-hydroxyandrostenedione and 9α-OH BN acid in the fermentation beer.

12. A process, according to claim 11, wherein said microorganism is cultivated in an aqueous nutrient medium under aerobic conditions in the presence of a mixture of two or more steroids wherein each steroid contains from 8 to 10 carbon atoms, inclusive, in the 17-alkyl side chain.

13. A process, according to claim 11, wherein said steroid is selected from the group consisting of sitosterol, cholesterol, stigmasterol, and campesterol.

14. A process, according to claim 12, wherein said steroid mixture is selected from the group consisting of sitosterol, cholesterol, stigmasterol, and campesterol.

15. A process for preparing 9α-hydroxy BN acid which comprises:
a. cultivating *Mycobacterium fortuitum* NRRL B-8119 in an aqueous nutrient medium under aerobic conditions in the presence of a steroid containing from 8 to 10 carbon atoms, inclusive, in the 17-alkyl side chain to produce 9α-hydroxyandrostenedione and 9α-hydroxy BN acid in the fermentation beer,
b. filtering said fermentaton beer to give a filtrate,
c. extracting said filtrate with butyl acetate at a pH of about 4.0 to give an extract,
d. washing said extract with a 5% sodium bicarbonate solution to give a wash solution,
e. extracting said wash solution with butyl acetate to give an extract, and
f. crystallizing 9α-hydroxy BN acid from said extract by concentration of the extract.

* * * * *

UNITED STATES PATENT OFFICE
CERTIFICATE OF CORRECTION

Patent No. 4,029,549         Dated June 14, 1977

Inventor(s) Frederick J. Antosz, Willard J. Haak and Merle G. Wovcha

It is certified that error appears in the above-identified patent and that said Letters Patent are hereby corrected as shown below:

Column 1, line 30, for "prepartion" read -- preparation --;
line 58, for "M, rhodochrous" read -- M. rhodochrous --.
Column 2, line 7, for "accmulate" read -- accumulate --.
Column 4, line 35, for "Prepgration" read -- Preparation --;
line 37, for "Mutagenes is" read -- Mutagenesis --. Column 6,
line 27, for "ethyl acetatecyclohexane" read -- ethyl acetate-
cyclohexane --. Column 7, line 67, for "AC" read -- AD --.
Column 9, line 4, claim 2, for "on an" read -- to an --;
lines 23-24, claim 7, for "nitrient" read -- nutrient --;
line 30, claim 8, for "cempersterol" read -- campesterol --;
line 33, claim 9, for "cempesterol" read -- campesterol.

Signed and Sealed this

Twentieth Day of September 1977

[SEAL]

Attest:

RUTH C. MASON
Attesting Officer

LUTRELLE F. PARKER
Acting Commissioner of Patents and Trademarks